(12) United States Patent
Liang et al.

(10) Patent No.: US 11,915,401 B2
(45) Date of Patent: Feb. 27, 2024

(54) APRIORI GUIDANCE NETWORK FOR MULTITASK MEDICAL IMAGE SYNTHESIS

(71) Applicant: SHENZHEN INSTITUTES OF ADVANCED TECHNOLOGY, Shenzhen (CN)

(72) Inventors: Dong Liang, Shenzhen (CN); Zhanli Hu, Shenzhen (CN); Hairong Zheng, Shenzhen (CN); Xin Liu, Shenzhen (CN); Qingneng Li, Shenzhen (CN); Yongfeng Yang, Shenzhen (CN)

(73) Assignee: SHENZHEN INSTITUTES OF ADVANCED TECHNOLOGY, Shenzhen (CN)

( * ) Notice: Subject to any disclaimer, the term of this patent is extended or adjusted under 35 U.S.C. 154(b) by 480 days.

(21) Appl. No.: 17/284,794

(22) PCT Filed: Dec. 9, 2020

(86) PCT No.: PCT/CN2020/135021
§ 371 (c)(1),
(2) Date: Apr. 13, 2021

(87) PCT Pub. No.: WO2022/120661
PCT Pub. Date: Jun. 16, 2022

(65) Prior Publication Data
US 2023/0031910 A1      Feb. 2, 2023

(51) Int. Cl.
*G06T 5/50* (2006.01)
*G06T 7/00* (2017.01)
*G16H 30/40* (2018.01)

(52) U.S. Cl.
CPC ............. *G06T 5/50* (2013.01); *G06T 3/4046* (2013.01); *G06T 7/0012* (2013.01); *G16H 30/40* (2018.01);
(Continued)

(58) Field of Classification Search
CPC .......... G06N 3/045; G06N 3/08; G06N 20/20; G06N 3/047; G06N 3/084; G06N 5/04;
(Continued)

(56) References Cited

U.S. PATENT DOCUMENTS 11,270,446 B2 * 3/2022 Liao .......................... G06T 7/55
11,599,980 B2 * 3/2023 Arroyo ..................... G06T 5/50
(Continued)

FOREIGN PATENT DOCUMENTS

CN    109636742 A    4/2019
CN    110580695 A    12/2019
(Continued)

OTHER PUBLICATIONS

X. Liu, A. Yu, X. Wei, Z. Pan and J. Tang, "Multimodal MR Image Synthesis Using Gradient Prior and Adversarial Learning," in IEEE Journal of Selected Topics in Signal Processing, vol. 14, No. 6, pp. 1176-1188, Oct. 2020, doi: 10.1109/JSTSP.2020.3013418. (Year: 2020).*

(Continued)

*Primary Examiner* — Ian L Lemieux
(74) *Attorney, Agent, or Firm* — Bayramoglu Law Offices LLC

(57) ABSTRACT

An apriori guidance network for multitask medical image synthesis is provided. The apriori guidance network includes a generator and a discriminator, wherein the generator includes an apriori guidance module configured to convert an input feature map into a target modal image pointing to a target domain according to an apriori feature, and the apriori feature is a deep feature of the target modal image. The generator is configured to generate a corresponding target domain image by taking the apriori feature of the target modal image and source modal image data as an input.

(Continued)

The discriminator is configured to discriminate an authenticity of the target domain image outputted by the generator.

8 Claims, 4 Drawing Sheets

(52) U.S. Cl.
CPC ........... *G06T 2207/10081* (2013.01); *G06T 2207/10088* (2013.01); *G06T 2207/10104* (2013.01); *G06T 2207/20076* (2013.01); *G06T 2207/20081* (2013.01); *G06T 2207/20084* (2013.01); *G06T 2207/20212* (2013.01); *G06T 2207/30004* (2013.01)

(58) Field of Classification Search
CPC ........ G06N 20/10; G06N 3/048; G06N 3/082; G06N 3/088; G06N 5/01; G06N 5/025; G06N 7/01; G06T 2207/10088; G06T 2207/20081; G06T 7/0012; G06T 2207/10044; G06T 5/003; G06T 5/009; G06T 2207/10104; G06T 2207/20084; G06T 2207/20221; G06T 5/50; G06T 2207/10081; G06T 2207/30016; G06T 3/4053; G06T 5/002; G06T 2207/20076; G06T 2207/20212; G06T 2207/30004; G06T 3/4046; G16H 30/40; A61B 6/032; A61B 6/5247; A61N 5/1039; A61N 2005/1055; G06V 30/194; G06V 10/764; G06V 10/82

See application file for complete search history.

(56) References Cited

U.S. PATENT DOCUMENTS

| | | | | |
|---|---|---|---|---|
| 2017/0372193 | A1* | 12/2017 | Mailhe | G06T 5/005 |
| 2018/0247201 | A1* | 8/2018 | Liu | G06T 1/00 |
| 2019/0049540 | A1 | 2/2019 | Odry et al. | |
| 2019/0220977 | A1* | 7/2019 | Zhou | G06T 7/0014 |
| 2019/0279075 | A1* | 9/2019 | Liu | G06N 3/045 |
| 2019/0318474 | A1 | 10/2019 | Han | |
| 2020/0034948 | A1 | 1/2020 | Park et al. | |
| 2020/0184660 | A1* | 6/2020 | Shi | G06T 7/30 |
| 2022/0180602 | A1* | 6/2022 | Hao | G06T 11/00 |
| 2022/0318956 | A1* | 10/2022 | Xu | G06T 11/008 |

FOREIGN PATENT DOCUMENTS

| | | | | |
|---|---|---|---|---|
| CN | 111814891 A | | 10/2020 | |
| WO | WO-2021022752 A1 * | | 2/2021 | G06K 9/6256 |

OTHER PUBLICATIONS

Guoyang Xie et al. "Cross-Modality Neuroimage Synthesis: A Survey". 2023. https://arxiv.org/abs/2202.06997 (Year: 2023).*

Xue Dong, et al., Synthetic CT Generation from Non-attenuation Corrected PET Images for Whole-body PET Imaging, Physics in Medicine & Biology, 2019, pp. 1-17.

Donghwi Hwang, et al., Generation of PET attenuation map for whole-body time-of-flight 18FFDG PET/MRI using a deep neural network trained with simultaneously reconstructed activity and attenuation maps, Journal of Nuclear Medicine, 2019, pp. 1-27.

Wen Li, et al., Magnetic resonance image (MRI) synthesis from brain computed tomography (CT) images based on deep learning methods for magnetic resonance (MR)-guided radiotherapy, Quant Imaging Med Surg, 2020, pp. 1223-1236, 10(6).

Dong Guoya, et al., Cross-modality medical image synthesis based on deep learning, Chinese Journal of Medical Physics, 2020, pp. 1335-1339, vol. 37 No. 10.

* cited by examiner

APRIORI GUIDANCE NETWORK FOR MULTITASK MEDICAL IMAGE SYNTHESIS

CROSS REFERENCE TO THE RELATED APPLICATIONS

This application is the national stage entry of International Application No. PCT/CN2020/135021, filed on Dec. 9, 2020, the entire contents of which are incorporated herein by reference.

TECHNICAL FIELD

The present disclosure relates to the field of medical image processing technologies, and more particularly, to an apriori guidance network for multitask medical image synthesis.

BACKGROUND

Medical image synthesis has important significance for obtaining images of different modalities. For example, positron emission tomography (PET) is a non-invasive imaging detection method for obtaining tomographic images of patients' bodies through computers and photon beams generated by positron annihilation. As a functional imaging technology different from computed tomography (CT), PET imaging can clearly and intuitively reflect relevant information of diseased tissues of human bodies, which is of great significance for clinical lesion detection. However, PET scanned images are lower in spatial resolution and poorer in image quality, and often fail to clearly show anatomical structure information of various parts of the human bodies. Therefore, the PET imaging technology is often used in conjunction with the CT imaging or MRI imaging technology to form a popular PET/CT or PET/MRI imaging system currently available on the market.

However, the introduction of CT or MRI will bring new problems. Specifically, for the CT imaging, a large amount of X-ray irradiation will cause a cumulative effect of radiation dose received by the human bodies, which may significantly increase the probability of occurrence of various diseases, thus having a negative effect on physiological functions of the human bodies. The MRI imaging may greatly extend data collection time and increase the patients' discomfort during scanning. In addition, CT modality images and MRI modality images can provide complementary information to each other, which is helpful for doctors' clinical diagnosis. Therefore, sometimes it is necessary to perform the CT scan imaging and MRI scan imaging for the patients separately, which leads to substantial increase of the patients' medical expenses and spending.

In the existing technologies, there are following technical solutions for generating CT images and MRI images.

Dong et al. published an article "*Synthetic CT generation from non-attenuation corrected PET images for whole-body PET imaging*" in Physics in Medicine & Biology in 2019. Non-attenuation corrected original PET images are successfully converted into CT modality images using cycle generative adversarial networks (CycleGAN). Pseudo CT images generated not only can provide the anatomical structure information to assist in the localization and diagnosis of lesion areas, but also can perform attenuation correction on the original PET images.

Donghwi Hwang et al. published an article "*Generation of PET attenuation map for whole-body time-of-flight 18F-FDG PET MRI using a deep neural network trained with simultaneously reconstructed activity and attenuation maps*" in the Journal of Nuclear Medicine. Image mapping from PET images to attenuation-corrected images is implemented using end-to-end U-Net networks. In the PET/MRI imaging system, the attenuation-corrected images are derivatives of the MRI images. This indicates that the conversion from the PET images to the MRI images has great feasibility. In recent years, many feasible solutions have been discussed about the generation from the PET images to the MRI images, which reveals the great clinical significance of this work.

Wen Li et al. published an article "*Magnetic resonance image (MRI) synthesis from brain computed tomography (CT) images based on deep learning methods for magnetic resonance (MR)-guided radiotherapy*" in Quantitative Imaging In Medicine And Surgery. The conversion from brain CT images to the MRI images is implemented by using currently popular deep convolutional neural networks. For the PET-MRI image synthesis tasks, conversion from the PET images to the CT images and then to the MRI images is a feasible solution, but similar to all the MRI-CT image tasks, this solution first needs to overcome the problem of image registration between different modalities.

Upon analysis, to solve the multi-modal medical image synthesis task based on the PET images, at present, generally three solutions are used as below.

1) Joint Multitask Learning

The objective task is to implement the generation from the PET images to the CT images and the MRI images. In this joint learning solution, the CT images and the MRI images are simultaneously generated using the single PET images. However, this solution requires cases and matched PET-CT-MR data pairs. However, experimental instruments capable of simultaneously performing PET scanning, MRI scanning and CT scanning are currently unavailable on the market. Therefore the data pairs cannot be obtained, and thus this solution is not available.

2) Serial Multitask Learning

The image generation task from the PET images to the CT images and the MRI images may be regarded as generation from the PET images to the CT images and then generation from the CT images to the MRI images. Such a two-step learning strategy can split a complex problem into a plurality of simple problems and solve them one by one. Both the generation from the PET images to the CT images and the generation from the CT images to the MRI images have been fully studied, and great progress has been made. However, this solution is apt to causing cumulative effects of errors, which greatly reduces final experimental effects. In addition, the split task of this solution also means that separate training data need to be collected for each subtask, which increases the workload of pre-tasks.

3) Integrated Multitask Learning

For "one-to-many" multitask learning, this task may be split into a plurality of subtasks according to output objects, such as the synthesis from the PET images to the CT images and the synthesis from the PET images to the MRI images. However, these subtask models generally have strong specificities, which severely limits the scope of application of these subtasks. For example, due to differences in data scanning instruments, the PET images of PET/CT scanning generally are much different from the PET images of PET/MRI scanning, so it is difficult to achieve good generation effects when the former is transferred to a PET-MRI model.

SUMMARY

An objective of the present disclosure is to overcome the above defects of the existing technologies by providing an apriori guidance network for multitask medical image synthesis.

According to a first aspect of the present disclosure, there is provided an apriori guidance network for multitask medical image synthesis. This network includes a generator and a discriminator, wherein the generator includes an apriori guidance module configured to convert an input feature map into a target modal image pointing to a target domain according to an apriori feature, and the apriori feature is a deep feature of the target modal image. The generator is configured to generate a corresponding target domain image by taking the apriori feature of the target modal image and source modal image data as input. The discriminator is configured to discriminate authenticity of the target domain image outputted by the generator.

According to a second aspect of the present disclosure, there is provided a method for multitask medical image synthesis. The method includes:
training, based on a generative adversarial mechanism, the provided apriori guidance network for multitask medical image synthesis; and
inputting source modal image data and an apriori feature of a target modal image into a trained generator to synthesize a corresponding target modal image.

Compared with the existing technologies, the present disclosure has an advantage of providing an apriori guidance network for multitask medical image synthesis to achieve image synthesis from one modal image to other multi-modal images. For example, by making full use of feature information of a PET scanning image, accurate image conversion from a PET image to a CT image or from the PET image to an MRI image under the guidance of a CT apriori feature or an MRI apriori feature is implemented.

Other features and advantages of the present disclosure will become apparent from the following detailed description of exemplary embodiments of the present disclosure with reference to accompanying drawings.

BRIEF DESCRIPTION OF THE DRAWINGS

The accompanying drawings herein are incorporated in and constitute a part of this specification, illustrate embodiments of the present disclosure and, together with the specification, serve to explain the principles of the present disclosure.

DETAILED DESCRIPTION OF THE EMBODIMENTS

Figure 1:
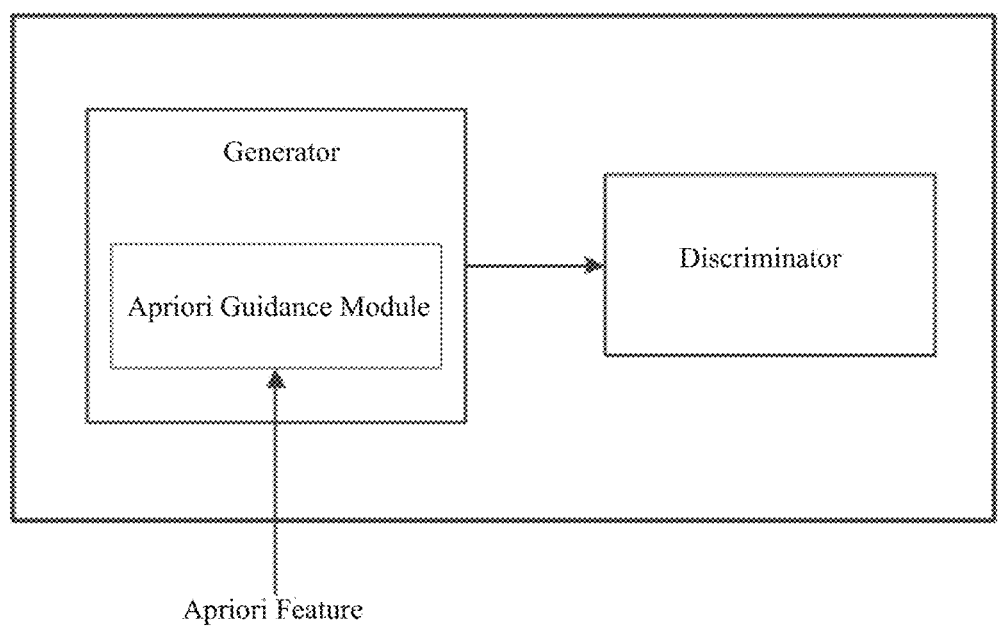
FIG. 1 is a structural diagram of an apriori guidance network for multitask medical image synthesis according to one embodiment of the present disclosure.

Various exemplary embodiments of the present disclosure will now be described in detail with reference to the accompanying drawings. It is to be noted that the relative arrangement, numerical expressions, and numerical values of the components and steps set forth in these embodiments do not limit the scope of the present disclosure unless otherwise specifically stated.

The following description of at least one exemplary embodiment is actually merely illustrative, and in no way serves as any limitation on the present disclosure and application or use thereof.

Technologies, methods and equipment known to those of ordinary skill in the related art may not be discussed in detail, but where appropriate, the technologies, methods and equipment should be considered as part of the specification.

In all examples shown and discussed herein, any specific values should be interpreted as merely exemplary and not limiting. Therefore, other examples of the exemplary embodiment may have different values.

It is to be noted that similar reference numerals and letters indicate similar items in the following accompanying drawings. Therefore, once an item is defined in one drawing, there is no need to discuss this item further in subsequent drawings.

The present disclosure provides an apriori guidance network for multitask medical image synthesis. With reference to FIG. 1, in short, this network includes a generator and a discriminator. The generator includes an apriori guidance module configured to convert an input feature map into a target modal image pointing to a target domain according to an apriori feature, and the apriori feature is a deep feature of the target modal image. The generator is configured to generate a corresponding target domain image by taking the apriori feature of the target modal image and source modal image data as input. The discriminator is configured to discriminate authenticity of the target domain image outputted by the generator. By using the present disclosure, image conversion from one modal image (or called source modal image) to other multi-modal (or called target modal) images can be achieved. For clarity, a description is made below by taking an example where a PET image serves as the source modal image and an MRI image or a CT image serves as the target modal image.

To ensure that the PET image still can be generated into the MRI or CT image corresponding to the PET image without a supervised sample, the present disclosure designs an apriori guidance network based on an alternate learning strategy. On the basis of a generative adversarial model (GAN), a plurality of apriori guidance modules are added into this network to achieve alternate learning of a plurality of tasks and to further improve quality of the image generated.

Specifically, the provided apriori guidance network generally includes three processes as below. In the first process, image apriori features are selected. The expression of the apriori features may be continuous or discrete, but all these apriori features conform to a certain distribution. For example, the apriori features include onehot encoding and variational autoencoding (VAE) hidden variable features. In the second process, a self-adaptive apriori guidance module is designed. Inspired by batch normalization and instance normalization, it is found that scale and bias of a convolutional feature map of an image have a marked impact on a final experimental result. Therefore, the scale and the bias of each convolutional feature map may be calculated by using the apriori feature of an input image, such that the feature map is fitted and mapped to the target domain image. In the third process, alternate learning of the generative network is carried out. The entire apriori guidance network adopts a generative adversarial mechanism, wherein the generator is based on a residual Unet network, introduces a plurality of apriori guidance modules, and adopts the alternate learning strategy to guide the network to generate a corresponding target image domain according to the received apriori feature. The selected apriori feature has a certain distribution, and thus stability and robustness of a generated result are guaranteed.

Operation steps of the apriori guidance network for multitask medical image synthesis provided by the present disclosure are as below.

In Step S1, apriori features of an image are selected.

For medical images of different modalities, apriori features of these medical images should have significant differences to ensure that the apriori features can effectively guide the direction of network training and generate a desired target modal image. In addition to specificity between different modalities, the apriori features of the image are also required to have the same distribution in the same modal. It is worth mentioning that the same distribution may be arbitrary, either a discrete distribution (such as one hot encoding or binary encoding) or a continuous distribution (such as a normal distribution). Semantically, the apriori features of the image may be understood as deep features of the target modal image, including anatomical structure information of an image modal. Thus, by introducing this apriori information into the network of the present disclosure, image generation quality of the network can be further improved.

Figure 2:
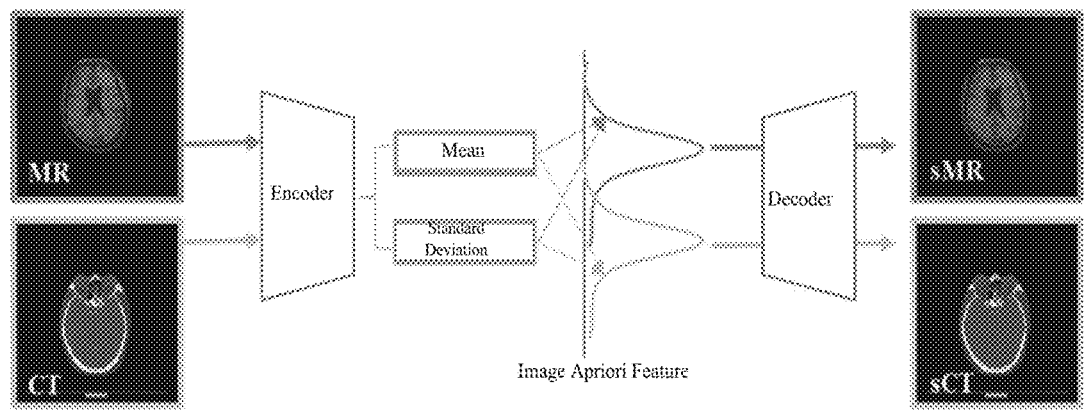
FIG. 2 is a schematic diagram of extracting an image apriori feature by using a variational autoencoder according to one embodiment of the present disclosure.

As shown in FIG. 2, in this embodiment, a variational autoencoder (VAE) is employed to extract the apriori features of different modal images. Different from a conventional autoencoder (AE), the VAE model first encodes the target modal image (CT or MRI image), wherein an encoded feature vector is split into two parts having the same length, respectively representing a mean μ and a standard deviation σ of the normal distribution. The image apriori feature in conformity with the normal distribution having the mean of μ and the standard deviation of σ may be restored therefrom according to a reparameter trick. After being processed by the decoder, the apriori feature may be reconstructed into an original input image (marked as sCT or sMR). To meet the specificity of the image apriori feature, the mean of CT modalities of an encoding is $\mu_{CT} \to 0$, and the mean of MR modalities of the encoding is $\mu_{MR} \to 10$. Furthermore, to ensure a generation capability of the VAE model, the standard deviation of the encoding is $\mu_{CT} \to 1$, $\sigma_{MR} \to 1$. That is, for the CT modalities, the apriori features conform to the standard normal distribution; and for the MR modalities, the apriori features conform to the normal distribution with a mean of 10 and a standard deviation of 1.

In Step S2, a self-adaptive apriori guidance module is designed.

Inspired by operations such as the batch normalization, preferably, the final generation direction of the network is guided by controlling the scale and the spatial bias of a convolutional feature map.

Figure 3:
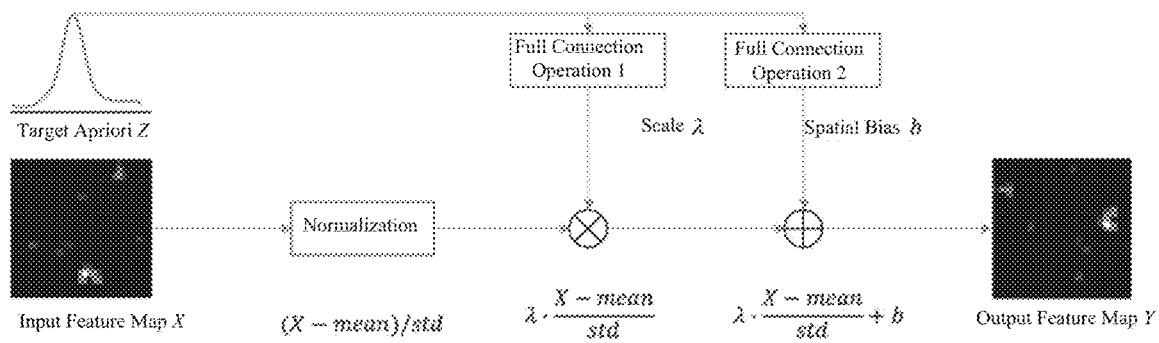
FIG. 3 is a schematic diagram of a self-adaptive apriori guidance module according to one embodiment of the present disclosure.

As shown in FIG. 3, input of the apriori guidance module is a feature map X with a size of H×W×C and a target apriori feature Z with a length of L. First, the inputted convolutional feature map is normalized (subtraction of the mean, and then divided by the standard deviation), which is expressed as:

$$X' = \frac{X - \text{Mean}(X)}{STD(X)} \tag{1}$$

Next, the inputted apriori feature undergoes two independent fully-connected operations f to obtain a scaled vector λ and a spatial biased vector b both having a length of C, which are expressed as.

$$\lambda = f_1(Z)$$

$$b = f_2(Z) \tag{2}$$

Finally, the normalized feature map is multiplied by the scaled vector along a channel direction, and the numeric obtained by the multiplication plus the spatial bias along the channel direction to obtain an output feature map pointing to the target domain, which is expressed as:

$$Y = \lambda \cdot X' + b \tag{3}$$

In Step S3, the generator and the discriminator are designed.

To improve the quality of a generated image, a generative adversarial mechanism is adopted. The generator is based on a residual Unet network, and a plurality of apriori guidance modules are introduced in the decoding part to implement the mapping of a PET image to a specified target modality.

Figure 4:
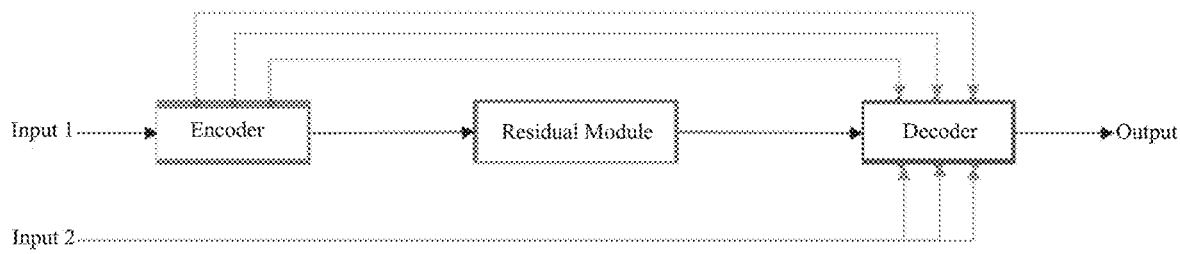
FIG. 4 is a schematic diagram of a generator network according to one embodiment of the present disclosure.

With reference to FIG. 4, the residual Unet network includes an encoder, a residual module, and a decoder. There exists a cross-over connection between the encoder and the decoder, which can solve a vanishing gradient problem and an exploding gradient problem in training, and can also promote information transfer between networks. Input 1 represents PET image data, and input 2 represents an apriori feature of a target modal image (CT or MRI image). After the inputted PET image is processed by the encoder, a multi-scale convolutional feature map is obtained. Next, the multi-scale convolutional feature map is transferred to the decoder containing a plurality of apriori guidance modules to generate the target modal image (CT or MRI image) as output under the guidance of the apriori feature of an input image.

Figure 5:
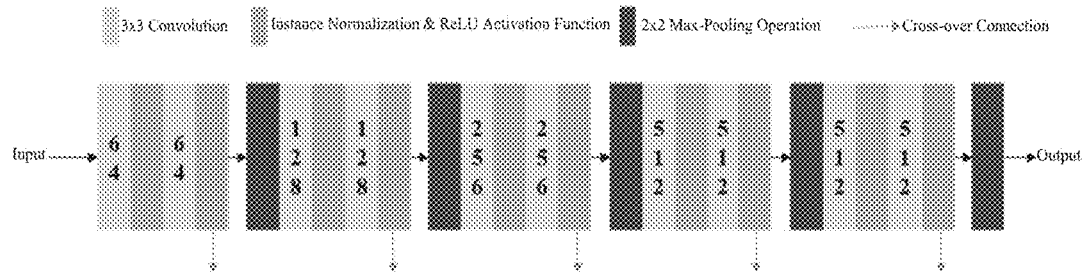
FIG. 5 is a schematic diagram showing details of an encoder network according to one embodiment of the present disclosure.

In one embodiment, the encoder as shown in FIG. 5 includes five convolutional modules. Except for the first convolutional module, each of the other convolutional modules is composed of one 2×2 max-pooling operation and two continuous and identical 3×3 convolutions. For example, all these convolutions have a step length of 1, followed by instance normalizations and ReLU activation functions. To retain more original image information, the max-pooling operation is removed from the first convolutional module. An encoding result of each of the convolutional modules is transferred to the decoder through a cross-over connection mechanism to better guide the generation from the PET image to the CT or MRI image. As an encoding depth increases, a width of the convolutional module progressively increases from the initial number of channels of 64 to the number of channels of 512. The final encoding result of the convolutional module is down-sampled by 2 times and then is transferred to the residual module to further extract depth expression information of the image.

Figure 6:
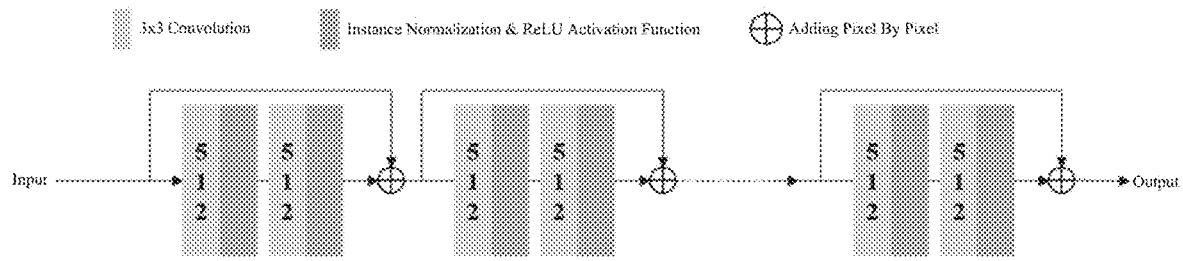
FIG. 6 is a schematic diagram showing details of a residual module network according to one embodiment of the present disclosure.

In one embodiment, the residual module is as shown in FIG. 6, and three continuous and identical residual modules are added between the encoder and the decoder. Each residual module contains two 3×3 convolutions having the step length of 1 and the number of channels of 512 and followed by the instance normalization and the ReLU activation function. An output result of each residual module is obtained by adding a pixel level of input of a first convolution and a pixel level of output of a second convolution together. The final output result of the residual module is transmitted to the decoder.

Figure 7:
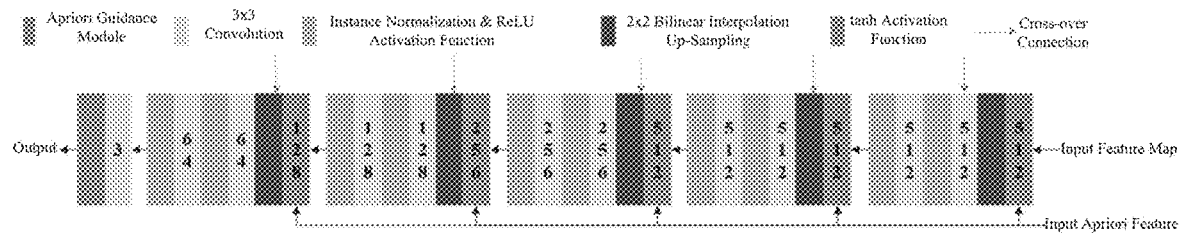
FIG. 7 is a schematic diagram showing details of a decoder network according to one embodiment of the present disclosure.

In one embodiment, as shown in FIG. 7, the decoder generally has a structure symmetrical to the encoder. The decoder differs from the encoder in that the 2×2 max-pooling operation of each convolutional module is replaced in the decoder with a bilinear interpolation up-sampling operation having a step length of 2. The feature map obtained by the residual module is decoded by four continuous convolutional modules. With the help of the cross-over connection, the decoded feature map processed by up-sampling can be merged with an encoded feature map having the corresponding resolution along the channel, and then the convolution is carried out. A final decoding result of the convolutional module is transferred to the last convolutional layer to generate a three-channel output image (CT or MRI image). The output image is constrained within an interval (−1, 1) by a tanh activation function. However, different from the traditional Unet network, in the decoder of the present disclosure, one self-adaptive apriori guidance module is added before each up-sampling operation to adjust a decoding direction of the convolutional feature map through the inputted apriori feature of the target modal. In this way, the generation from the PET image to the target modal image is achieved.

Figure 8:
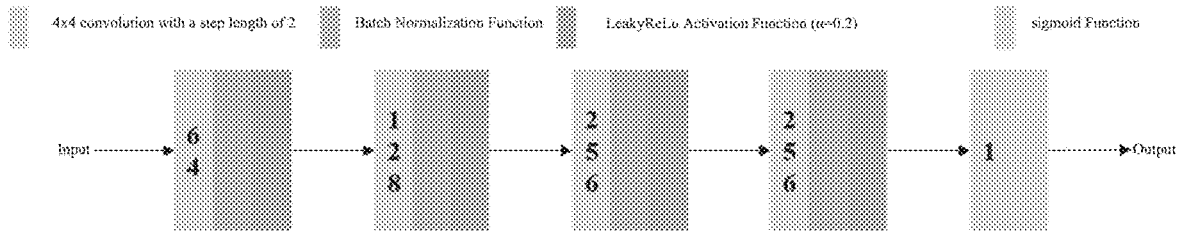
FIG. 8 is a schematic diagram of a discriminator network according to one embodiment of the present disclosure.

For the discriminator of the apriori guidance network, in one embodiment, a fully convolutional network structure is employed to determine the authenticity of the generated image. As shown in FIG. 8, the discriminator has four convolutional layers and a final output layer. Each of the four convolutional layers contains a 4×4 convolution with a step length of 2, a batch normalization, and a LeakyReLu activation function with a slope of 0.2. The numbers of convolution kernels of the four convolution layers are 64 channels, 128 channels, 256 channels and 256 channels, respectively. In the final output layer, a probability scalar within one interval (0, 1) is generated to discriminate authenticity of an input image. If the input image is true, the probability scalar is close to 1; and if the input image is false, the probability scalar is close to 0.

In Step S4, a multi-target image is generated by using the alternate learning strategy.

For example, two sets of PET scanning data are collected, namely: a PET/CT data set and a PET/MRI data set. Compared with other common methods that generally two data sets are transferred to a model for training independently, in some embodiments of the present disclosure, the PET/CT data set is marked as domain 1, and the PET/MRI data set is marked as domain 2. Next, the two data sets are fully mixed to construct one larger data set with a "domain mark". According to the "domain mark" of the larger data set, apriori distribution of the input network may be determined.

For the case where it is required to achieve the multitask image synthesis of simultaneously generating CT and MRI images from PET images, apparently, the task of generating the CT image from the PET image and the task of generating the MRI image from the PET image have great repeatability. Preferably, the apriori guidance module is employed to store parameters representative of a non-repetitive part between the two tasks, and a repetitive part therebetween is stored in other parts of the generator. Each time when the PET image having different "domain marks" is inputted, the parameters of the apriori guidance module is updated, such that alternate training from the PET image to the CT image and from the PET image to the MRI image is achieved.

In summary, to overcome the problem of image registration between different data (PET/CT and PET/MRI), by using the above-mentioned alternate learning method, the generation of an unlabeled image is implemented. Even if only PET/CT scanning is performed on a patient, a high-quality MRI image can be generated by using the scanned PET image and the priori Informatio of the MRI image according to the present disclosure, and vice versa.

In Step S5, a joint loss function is designed.

To improve the quality and stability of an image generated by the network, a more complex joint loss function is designed to optimize the iterative training of the network and further ensure that the generated MRI or CT image can meet needs of most clinical medical diagnoses.

In one embodiment, the designed joint loss function includes a mean absolute error loss function ($L_{MAE}$), a perceptive loss function ($L_{PCP}$), and unsaturated adversarial loss functions ($L_{GAN}^G$ and $L_{GAN}^D$) which is, for example, expressed as:

$$L_{comb}=L_{MAE}+\lambda_1 \cdot L_{PCP}+\lambda_2 \cdot L_{GAN}^G \qquad (4)$$

wherein the mean absolute error function $L_{MAE}$ reflects a difference between a generated image and a reference image at a pixel level; and the perceptive loss function $L_{PCP}$ reflects a difference between the generated image and the reference image at a feature level. In the perceptive loss function $L_{PCP}$ of the present disclosure, a VGG19 network pre-trained on an ImageNet data set is used as a feature extractor to extract various scale features of the generated image and the reference image, and to measure a difference therebetween. The adversarial loss function $L_{GAN}^G$ of the generator represents a cross entropy that the discriminator discriminate the generated image as true. The smaller the entropy is, the more authentic the generated image is. $\lambda_1$ and $\lambda_2$ represent a weight coefficient of the corresponding function, respectively. The above three functions are specifically expressed as follows:

$$L_{MAE}=E[y-G(x)] \qquad (5)$$

$$L_{LPC}=\Sigma_i^n E[\phi_i(y)-\phi_i(G(x))] \qquad (6)$$

$$L_{GAN}^G=E[\log(D(G(x))] \qquad (7)$$

wherein x represents the PET image inputted by a model, y represents a corresponding target reference image (CT or MRI image), G represents the generator of the model, D represents the discriminator of the model, E represents a mathematical expectation, $\phi_i$ represents an $i^{th}$ encoded convolutional layer of a VGG19 model, and n represents number of selected convolutional layers.

According to the generative adversarial mechanism, when the generated image can mislead the discriminator to make an authenticity discrimination probability close to 1, the generated image is authentic and convincing. In another aspect, fidelity of the generated image is also related to an authenticity discrimination capability of the discriminator. The more powerful the authenticity discrimination capability of the discriminator is, the more authentic the generated image successfully fooling the generator is. Therefore, an iterative optimization is performed on a loss function constructed for the discriminator D. The loss function of the discriminator is as follows:

$$L_{GAN}^D = E[\log(D(y)) + \log(1 - D(G(x)))] \quad (8)$$

Uniform distribution at the feature level can be achieved no matter for the adversarial loss function of the generative adversarial model or the introduced perceptive loss function. This not only can generate a more authentic image, but also can significantly speed up the convergence speed of the network. To balance the contribution of each loss function during the training of the apriori guidance network, for example, $\lambda_1$ and $\lambda_2$ are respectively set to 1.0 and 0.01 according to experience. In fact, according to several experiments, minor adjustment of these loss weights does not have great impact on the training of the network.

In Step S6, the apriori guidance network is optimized and trained with the objective of preset loss functions.

For example, during the training process, a pair of images are selected from the PET/CT data set and the PET/MRI data set respectively, the PET image is used as input of the network, the CT image or the MRI image is used as a reference, and optimized training is carried out using an RMSProp optimizer until a convergent state is gradually reached.

Further, by using the trained generator, any PET image may be synthesized in real time to obtain a CT modality image and/or an MRI image.

Figure 9:
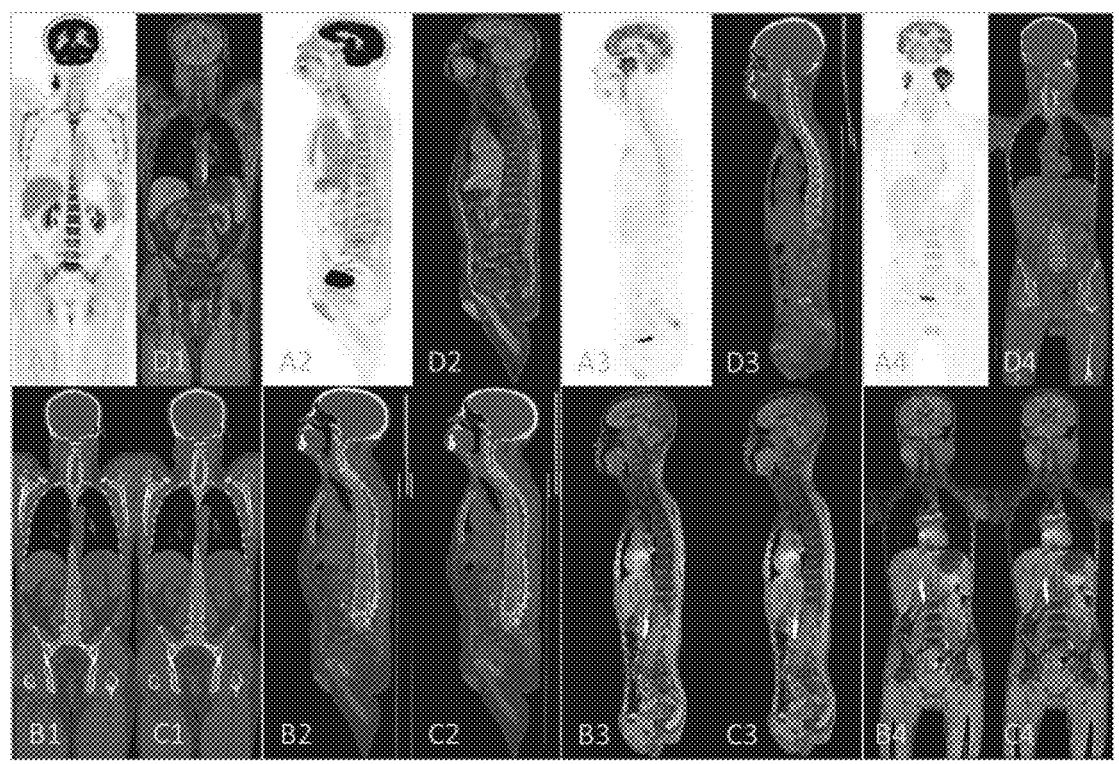
FIG. 9 is a schematic diagram showing an experimental result according to one embodiment of the present disclosure.

To further verify effects of the present disclosure, an experimental simulation is carried out, and results are as shown in FIG. 9. (A1, A2, A3, A4) represent inputted PET images; (B1, B2, B3, B4) represent reference domain images corresponding to the inputted images; (C1, C2, C3, C4) represent reference domain images generated in a supervised network; and (D1, D2, D3, D4) represent non-reference domain images generated in an unsupervised network. As can be seen, the present disclosure not only can generate a high-quality reference domain image (which has been subjected to image registration with the inputted PET image and comes from the same scanning data pair) under a supervised state, but also can generate a convincing non-reference domain image under an unsupervised state.

In summary, compared with the existing PET-CT generation task and the PET-MRI generation task, beneficial effects of the present disclosure are embodied in the following. First, the unsupervised generation from a PET image to a CT/MRI image is achieved by using the alternate learning strategy and the apriori guidance module and by making full use of a large amount of repetitive work between the two generation tasks. For the PET-CT data set, the present disclosure can achieve the generation from the PET image to a corresponding MRI modality image in case of lack of MRI reference images. Similarly, for a PET-MRI data set, the present disclosure can achieve the generation from the PET image to a CT modality image in the absence of a CT reference image. Moreover, in the present disclosure, apriori distribution information of a target modality is also combined with a conventional generative network, which significantly improves detail expressiveness and stability of the generated image. Furthermore, in conjunction with multiple loss functions, quality of an output image is effectively guaranteed. Meanwhile, a plurality of residual modules are added between the encoder and the decoder of the network, which effectively increases the convergence speed of the network and improves training efficiency of the network.

It is to be noted that in addition to application in the generation from PET images to CT and MRI images, the alternate learning strategy and the apriori guidance module provided by the present disclosure may also be applied to other types of multi-modal image generation tasks. In addition to application in image generation tasks, a method of combining apriori information and the network can also be widely used in other image tasks to further improve accuracy of experimental results and enhance stability of network training. As a plug-and-play module, the apriori guidance module may be added into any multitask neural convolutional network workflow, which makes full use of the repetitive work between multiple tasks to greatly reduce a parameter scale of a network model, and ensures efficiency of the network.

It is to be understood that the above-mentioned embodiments are merely exemplary, and those skilled in the art can make appropriate modifications or variations without departing from the spirit and scope of the present disclosure, for example, using different numbers of convolutional layers, convolution step lengths, convolution kernel sizes, and different activation functions, etc. For another example, the apriori guidance module does not have to be arranged for all up-sampling operations of the decoder.

The present disclosure may be a system, a method, and/or a computer program product. The computer program product may include a computer readable storage medium having computer readable program instructions thereon for causing a processor to carry out aspects of the present disclosure.

The computer readable storage medium may be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. More specific examples (a non-exhaustive list) of the computer readable storage medium include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. The computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may include copper transmission cables, optical fiber transmission, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

The computer program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Smalltalk, C++, or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In a scenario involved with the remote computer, the remote computer may be coupled to the user's computer through any type of network, including a local area network (LAN) or a wide area network (WAN), or may be coupled to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described with reference to flowcharts and/or block diagrams according to the method, apparatus (system) and a computer program product of the embodiments of the present disclosure. It is to be understood that each block of the flowcharts and/or block diagrams, and combinations of blocks in the flowcharts and/or block diagrams, can be implemented by the computer readable program instructions.

These computer readable program instructions may be provided to a processor of a general purpose computer, special purpose computer, or other programmable data processing apparatus to produce a machine, such that these instructions, which execute via the processor of the computer or other programmable data processing apparatus, create means for implementing the functions/acts specified in one or more blocks in the flowcharts and/or block diagrams. These computer readable program instructions may also be stored in a computer readable storage medium that can direct a computer, a programmable data processing apparatus, and/or other devices to function in a particular manner, such that the computer readable medium having instructions stored therein includes an article of manufacture including instructions which implement aspects of the functions/acts specified in one or more blocks in the flowcharts and/or block diagrams.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in one or more blocks in the flowcharts and/or block diagrams.

The flowcharts and block diagrams in the accompanying drawings illustrate architectures, functions and operations of possible implementations of systems, methods, and computer program products according to a plurality of embodiments of the present disclosure. In this regard, each block in the flowcharts or block diagrams may represent a module, a program segment, or a portion of instructions, which includes one or more executable instructions for implementing the specified logical function(s). In some alternative implementations, the functions denoted by the blocks may occur in a sequence different from the sequences shown in the accompanying drawings. For example, two blocks shown in succession may, in fact, be executed substantially concurrently, or the blocks may sometimes be executed in a reverse sequence, depending upon the functions involved. It is also to be noted that each block in the block diagrams and/or flowcharts and/or a combination of the blocks in the block diagrams and/or flowcharts may be implemented by a special-purpose hardware-based system executing specific functions or acts, or by a combination of a special-purpose hardware and computer instructions. It is well known to those skilled in the art that implementations by means of hardware, implementations by means of software and implementations by means of software in combination with hardware are equivalent.

The descriptions of the various embodiments of the present disclosure have been presented above for purposes of illustration, but are not intended to be exhaustive or limited to the embodiments disclosed. Therefore, it is apparent to an ordinary skilled person in the art that modifications and variations could be made without departing from the scope and spirit of the embodiments. The terminology used herein is chosen to best explain the principles of the embodiments, the practical application or technical improvement over technologies found in the marketplace, or to enable others of ordinary skill in the art to understand the embodiments disclosed herein. The scope of the present disclosure is limited by the appended claims.

What is claimed is:

1. A method for a multitask medical image synthesis, comprising:
   training, based on a generative adversarial mechanism, an apriori guidance network for the multitask medical image synthesis; and
   inputting source modal image data and an apriori feature, the apriori feature being a deep feature of a target modal image, into a trained generator to synthesize the target modal image;
   wherein the apriori guidance network comprises the generator and a discriminator, wherein the generator comprises an apriori guidance module configured to convert an input feature map into the target modal image pointing to a target domain according to the apriori feature; and
   wherein the generator is configured to generate a corresponding target domain image by taking the apriori feature of the target modal image and the source modal image data as an input; and the discriminator is configured to discriminate an authenticity of the corresponding target domain image outputted by the generator;
   wherein for the input feature map X having a size of H×W×C and the apriori feature Z having a length of L, the apriori guidance module is configured to generate the target modal image pointing to the target domain by:

normalizing the input feature map X to obtain a normalized feature map X', a normalization is expressed as:

$$X' = \frac{X - \text{Mean}(X)}{STD(X)},$$

processing the apriori feature Z by independent full connection operations $f_1$ and $f_2$ respectively to obtain a scaled vector λ and a spatial biased vector b both having a length of C, expressed as:

$\lambda = f_1(Z)$, $b = f_2(Z)$, and obtaining an output feature map pointing to the target domain by multiplying the normalized feature map X' by the scaled vector λ along a channel direction and plus the spatial biased vector b along the channel direction, expressed as:

$Y = \lambda \cdot X' + b$, wherein Mean represents a mean value, and STD represents a variance.

2. The method according to claim 1, wherein the generator comprises an encoder, a residual module, and a decoder connected in sequence, wherein a cross-over connection exists between the encoder and the decoder;
wherein the encoder is configured to convert the source modal image data into a multi-scale convolutional feature map; and wherein the decoder comprises a plurality of apriori guidance modules; and
wherein the decoder is configured to generate the target modal image as an output under a guidance of the apriori feature of an input image.

3. The method according to claim 2, wherein the encoder comprises a plurality of convolutional modules, a first convolutional module comprises a convolution operation, a second convolutional module of the encoder comprises a max-pooling operation and the convolution operation, an encoding result of the encoder is down-sampled to obtain a down-sampled encoding result, and the down-sampled encoding result is transferred to the residual module, the decoder adopts up-sampling corresponding to the encoder, and the apriori guidance module is arranged for each up-sampling operation.

4. The method according to claim 1, wherein the discriminator comprises a plurality of convolutional layers and an output layer, each of the plurality of convolutional layers comprising a convolution, a batch normalization, and an activation; and
wherein the output layer is configured to determine an authenticity of an input image based on a generated probability scalar.

5. The method according to claim 1, wherein the source modal image data is a positron emission tomography (PET) image, the target modal image is a computed tomography (CT) image and a magnetic resonance image (MRI) image, and the apriori guidance network is trained taking a specified joint loss function as an optimization objective by:

collecting a PET/CT data set and a PET/MRI data set, denoting a domain mark of the PET/CT data set as a first domain, and denoting a domain mark of the PET/MRI data set as a second domain;
mixing the PET/CT data set and the PET/MRI data set for constructing a mixed data set having the first domain mark and the second domain mark, and then determining a corresponding apriori feature according to a corresponding domain mark of the mixed data set; and
storing, by using the apriori guidance module, a parameter representative of a non-repetitive part between a CT image generation task and an MRI image generation task;
wherein when the PET image having different domain marks is inputted, a parameter of the apriori guidance module is updated, and an alternate training from a PET modality image to a CT modality image and from the PET modality image to an MRI modality image is achieved.

6. The method according to claim 5, wherein the specified joint loss function comprises a mean absolute error function $L_{MAE}$, a perceptive loss function $L_{PCP}$, and adversarial loss functions $L_{GAN}^G$ and $L_{GAN}^D$, expressed as:

$$L_{comb} = L_{MAE} + \lambda_1 \cdot L_{PCP} + \lambda_2 \cdot L_{GAN}^G,$$

$$L_{MAE} = E[y - G(x)],$$

$$L_{PCP} = \sum_i^n E[\phi_i(y) - \phi_i(G(x))],$$

$$L_{GAN}^G = E[\log(D(G(x)))],$$

$$L_{GAN}^D = E[\log(D(y)) + \log(1 - D(G(x)))],$$

wherein x represents the PET image inputted by a model, y represents a corresponding target reference image, G represents the generator, D represents the discriminator, E represents a mathematical expectation, $\phi_i$ represents an $i^{th}$ encoded convolutional layer of a VGG19 model, n represents a number of selected convolutional layers, $\lambda_1$ and $\lambda_2$ represent weight coefficients of corresponding functions, and $L_{GAN}^2$ represents a loss function of the discriminator.

7. The method according to claim 1, wherein the apriori feature of the target modal image is extracted by:
encoding the target modal image, wherein an encoded feature vector is split into two parts having a same length, respectively representing a mean μ and a standard deviation σ of a normal distribution; and
restoring the image apriori feature in conformity with the normal distribution having the mean of μ and the standard deviation of σ according to a reparameter trick.

8. A non-transitory computer readable storage medium, storing a computer program, wherein when the computer program is executed by a processor, the computer program implements the method according to claim 1.

* * * * *